US006376473B1

(12) United States Patent
Audonnet et al.

(10) Patent No.: US 6,376,473 B1
(45) Date of Patent: *Apr. 23, 2002

(54) POLYNUCLEOTIDE VACCINE FORMULA IN PARTICULAR AGAINST BOVINE RESPIRATORY PATHOLOGY

(75) Inventors: Jean-Christophe Audonnet; Annabelle Bouchardon, both of Lyons; Philippe Baudu, Craponne; Michel Riviere, Ecully, all of (FR)

(73) Assignee: Merial, Lyons (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/232,279

(22) Filed: Jan. 15, 1999

Related U.S. Application Data

(63) Continuation-in-part of application No. PCT/FR97/01325, filed on Jul. 15, 1997.

(30) Foreign Application Priority Data

Jul. 19, 1996 (FR) .............................. 96 09403

(51) Int. Cl.[7] .......................... C12N 15/45; C07H 21/04
(52) U.S. Cl. ...................... 514/44; 424/211.1; 424/813; 435/320.1; 536/23.72
(58) Field of Search ....................... 435/320.1; 514/44; 424/202.1, 204.1, 211.1, 229.1, 813; 536/23.72

(56) References Cited

U.S. PATENT DOCUMENTS 5,541,102 A * 7/1996 Donis et al. ............. 435/240.2
5,843,913 A   12/1998 Li et al.
6,019,980 A * 2/2000 Li et al. ................... 424/211.1

FOREIGN PATENT DOCUMENTS

| EP | 0661059 A2 | 7/1995 |
| WO | WO 92/01471 | * 2/1992 |
| WO | WO 93/14207 | 7/1993 |
| WO | WO 95/20660 | 8/1995 |

OTHER PUBLICATIONS

J.E. Crowe, Jr., "Current Approaches To The Development of Vaccines Against Disease Caused By Respiratory Syncytial Virus (RSV) and Parainfluenza Virus (PIV): A Meeting Report of The WHO Programme For Vaccine Development (Nyon, Switzerland)", Vaccine, vol. 13–4 (1995) pp. 415–421.
G.J.M. Cox, et al., "Bovine Herpesvirus 1: Immune Responses In Mice and Cattle Injected With Plasmid DNA", Journal of Virology, vol. 67 No. 9 (1993) pp. 5664–5667.
J. Hartikka, et al., "An Improved Plasmid DNA Expression Vector for Direct Injection Into Skeletal Muscle", Human Gene Therapy, vol. 7 No. 10 (1996) pp. 1205–1217.
Kurstak, E., et al., Modern Vaccinology, Plenum Medical Book Company, New York, pp. 13–23 and 41–54, 1994.*
Lerch et al., Journal of Virology, 64(11):5559–5569, Nov. 1990.*
Lerch et al., Virology 181:118–131, 1991.*
Babiuk et al., Annals New York Academy of Sciences 772:47–63, Nov. 1995.*
Yancey R.J., Journal of Dairy Science 76:2418–2436, Aug. 1993.*
Herbert et al., ed. The Dictionary of Immunology, 4th ed., Academic Press, London, p. 163, 1995.*

* cited by examiner

Primary Examiner—Brenda Brumback
(74) Attorney, Agent, or Firm—Frommer Lawrence & Haug, LLP; William S. Frommer; Thomas J. Kowalski

(57) ABSTRACT

Disclosed and claimed are compositions for inducing in a bovine host an immunological response against bovine respiratory syncytial virus or bovine viral diarrhea virus containing at least one plasmid that contains and expresses in vivo in a bovine host cell nucleic acid molecule(s) having sequence(s) encoding bovine respiratory syncytial virus F protein, or G protein, or F and G proteins; or, at least one plasmid that contains and expresses in vivo in a bovine host cell nucleic acid molecule(s) having sequence(s) encoding bovine viral diarrhea virus E2 protein, or C, E1 and E2 proteins, or E1 and E2 proteins. Methods and kits employing such compositions are also disclosed.

13 Claims, 15 Drawing Sheets

```
  1    ATGGCCGCTCGCGGTGTCTGAAGCGCCGGAGACGGTGGCGAGGACAGGT
  1  ▶ MetAlaAlaArgGlyGlyAlaGluArgAlaAlaGlyAlaAspGlyAlaArgGlyArgGlyGlnArg

64    CGTCATCTACGACCGGACGTGTTCGCTGCTCTACGGCCTGCTGGCCGGC
 22  ▶ ArgHisLeuArgProGlyArgValLeuAlaAlaLeuArgGlyProAlaAlaProGlyAlaGly

127    GGGGCGGCGCGCTAGCCGCTGCCCTGCTATGGGACGTGGCCTGCTGGCCG
 43  ▶ GlyAlaAlaArgAlaAlaLeuAlaLeuLeuTrpAlaThrTrpAlaLeuLeuAlaAla

190    CCCGCCGGGGCGACCGGCGACAACGCCCCCGGCGCGAAGAGGCCGAGCCCG
 64  ▶ ProAlaAlaGlyArgProAlaThrProAlaProProGluAlaAlaSerPro

253    GCGCCCCCCAGCCCCCAGCCCCGGCCCCGGGCCCGCCAGCCGCGACAAC
 85  ▶ AlaProProAlaSerProSerProProGlyProAspGlyAspAlaSerProAspAsn

316    AGCACAGACGTGGCCGCCCTCGCGCTGTCCCACGGTGTCGTGGTTCGCTTC
106  ▶ SerThrAspValAlaArgLeuAlaLeuAlaGlnLeuAlaLeuAlaGlyLeuAsnSerArgPhePhe

379    GTGTGCCCGCCCCCTCGGGCGGCACGGTGGTCGTGGCCGTGCCCTGAG
127  ▶ ValCysProProProSerGlyAlaThrValValAlaValLeuAlaProAlaArgProCysProGlu

442    TACGGGCTCGGCGAACTACACGGAGGCCATGGGTCATTACAAGGAGAACATCGCGCCG
148  ▶ TyrGlyLeuGlyArgAsnTyrThrGluGlyIleTyrLeuValIleTyrLysGluAsnIleAlaPro

505    TACACGTTCAAGGCCTACATTACAAAAACGTGATCGTGACCACCGCAGCACG
169  ▶ TyrThrPheLysAlaTyrIleTyrLysAsnValIleValThrThrThrTrpAlaGlySerThr
```

FIG. 2A

```
568   TACGCGGCCATTACAAACCAGTAGTACACGGACCGCGTGCCCGTGCATGGGCGAGATCACGGAC
190 ► TyrAlaAlaIleThrAspGlyTyrThrAspArgValProValGlyMetGlyIleThrAsp

631   CTGGTGACAAGAAGTGGCCACCTGCCTTTCGAAAGCCGAGTACCTGCGGGGCCAAGGTG
211 ► LeuValAspLysLysTrpArgCysLeuSerLysAlaGluTyrLeuArgSerGlyLysVal

694   GTGGCCTTTGACCGCGACGACGACCCCTGGGAGGCCCTGAAGCCTGCGGGCCTGAGCGCG
232 ► ValAlaPheAspArgAspAspAspProTrpGluAlaProLysLeuProAlaArgLeuSerAla

757   CCCGGGGTGCGGGGCCTGCACACGACGATGTGTACACGGACGATCGGCTCCGGGGCTC
253 ► ProGlyValArgGlyTrpHisThrThrAspAspValTyrThrAlaLeuGlySerAlaGlyLeu

820   TACCGCACGGGTCACCTCTGTGAACTGTGTGAAGAAGTGGAGGCGCTCGGTGTACCCG
274 ► TyrArgThrGlyThrSerValAsnCysIleValGluValGluAlaArgSerValTyrPro

883   TACGACTCGTTCGCGACCTCGCTCTGACCGGGGACATTATCTACATGTCGCCTTTTACGGGCTCGC
295 ► TyrAspSerPheAlaLeuSerThrGlyAspIleIleTyrMetSerProPheTyrGlyLeuArg

946   GAGGGCGCCACCGGAGCCTTCGCCGCCAGCAGATCGAGGGCTA
316 ► GluGlyAlaHisArgGluHisThrArgLeuLeuAlaLeuProAlaAspArgGlyLeu

1009  CTACAAGGCGGACATGCGCCCCTCAAGGAGCCGTCTCGCGAACTTTTGCG
337 ► LeuGlnAlaArgHisGlyHisGlyProGlyAlaProGlyAlaGlyLeuGluAlaPheAla

1072  TACACAGCACCTGACCGTAGCCTGGGTGCCCAAGCGCAAAAACGTGTCTCGCTGGC
358 ► TyrThrAlaArgAspGlySerLeuGlyLeuGlyAlaGlnLysAlaArgValAlaAlaGly
```

FIG. 2B

```
1135  CAAGTGGCCGAGGCGGACGAAATGCTGCGAGACGAGAGCCGGGAACTTCCGCTTCACGGC
 379▶ GlnValAlaArgGlyGlyArgAsnAlaAlaArgGluArgGluProArgGluLeuProLeuHisGly

1198  CCGCTCGCTCTCGGCGACCTTGTGAGCGACCACACCTTGCGGTTGCAGAATGTGCCGCT
 400▶ ProLeuAlaLeuGlyAspLeuValSerAspHisThrLeuArgLeuGlnAsnValAlaAla

1261  GAGCGACTGCGTGATCGAAGAGGCCGAGGCGGTGCTACGCGGCGCTTGTGTGGC
 421▶ GluArgLeuArgAspArgArgGlyArgGlyArgAlaArgLeuProArgAlaLeuGln

1324  CGGCACGCACGTGCTCGGGGCAGCTGGAGACGTACCTGCCAAGTGTACCGGCTGAGCTCGAAC
 442▶ ArgHisAlaArgHisValGlyGlnLeuGlyAspValProGlyAlaArgArgCysArgGly

1387  CTTCCGGCGATGCTCAGCAACGAGCTGGCCAAGCTGTACCTGGAGCAGCTGGCGCTCGAAC
 463▶ LeuProAlaMetLeuSerAsnGluLeuAlaLysLeuTyrLeuGluGlnLeuAlaArgSerAsn

1450  GGCACGCTCGAGGGCCTGTTCGCCGCCGCCCCCAAGCCGCCCAACGGGCCCCGCGCCCGC
 484▶ GlyThrLeuGluGlyLeuPheAlaAlaAlaProLysProProAsnGlyProArgAlaArg

1513  GCCGGCAGCTCTGCGGGTCTGGGGCTGCCGGCGCTCGCAGCAAGTGGCCCCGCCGGCCC
 505▶ AlaAlaProSerAlaProGlyLeuGlyProAlaAlaAlaSerGlyProAlaGlyAspAla

1576  GGCGGCGGGGTGACTACCGTGTCGAGCTCGGCCGAGTTGCCGAGTTCACCTACGACCAC
 526▶ GlyGlyArgValThrThrValSerSerAlaGluPheAlaAlaLeuGlnPheThrTyrAspHis

1639  ATCCAGGACCACGTGAACCATGTTCAGCCTTGGTGCCTCGTCCTGCTGCTCGCAGAAC
 547▶ IleGlnAspHisValAsnHisValGlnProTrpCysLeuValLeuLeuGlnAsn
```

FIG. 2C

```
1702  AAGGAGCCCCTGTGGCCGAGGCGGCTAAGCTCAACCCCAGGCGGCCAGGCTCCG
 568  LysGluArgAlaLeuTrpAlaGluAlaAlaLysLeuAsnProSerAlaAlaSerAlaAla

1765  CTGGACCGCCGCGCGGCGGCGGCCATGTTGGGGACGCCGTGACCGTACTGCCACGAG
 589  LeuAspArgArgAlaAlaAlaAlaArgMetLeuGlyAspAlaMetAlaValThrTyrCysHisGlu

1828  CTGGGCGAGGGGCGCGTGTTCATCGAGAACTCGATGAGCATGCGCGCCGGTTTGCTACAGC
 610  LeuGlyGluGlyArgValPheIleGluAsnSerMetArgAlaProGlyGlyValCysTyrSer

1891  CGCCCGCCGGTCTCCTTTGCCTTCGGCAACGAGAGCGGTGAGGCCGAGCTCGGCGAG
 631  ArgProProValSerPheAlaPheGlyAsnGluSerGluProValGluGlnLeuGlyGlu

1954  GACAACGAGCTGTGCCGCCGCTCGTGGAGCCCTGCGCCAACCACAAGGCTAC
 652  AspAsnGluLeuCysArgArgSerTrpSerProCysThrAlaAsnHisLysArgTyr

2017  TTCCGCTTTGGCTTTGCCGATCAGCGAGTACTACGAGAACTTTGTGGAAGTCTGAGACGCCGAG
 673  PheArgPheGlyAlaAspTyrValTyrTyrGluAsnLeuThrValGluArgProLeu

2080  GCGGAGCTGGAGGTGTACAAGTGTACACCGCCGACGAGCTCGCTCGACTACAGC
 694  AlaGluLeuGluValValIleSerThrPheValAspLeuAsnLeuThrValGluAspArgGlu

2143  TTCTTGCCGCTAGAAGTGTACACCGCCGACGAGCTCGCTCGACTACAGC
 715  PheLeuProGluValTyrThrArgAlaGluLeuAlaAspThrGlyLeuLeuAspTyrSer

2206  GAGATACAGCCGCCAACCAGCTGCACGAGCTCCGGTTCTACGACATTGACCGGTGTCAAG
 736  GluIleGlnArgArgAsnGlnLeuHisGluLeuArgPheTyrAspIleAspArgValLys
```

FIG. 2D

```
2269  ACGGACGGCAATATGGCCATCATGCGAGGCTCGCCAACTTCTTTCAGGGCCTGGGCCGTC
 757▶ ThrAspGlyAsnMetAlaIleMetArgGlyLeuAlaAsnPhePheGlnGlyLeuGlyAlaVal

2332  GGGCAGGCGGTGGCACGGTGGTGCTGGGCGCCGTCGGCGCTCTCGACCGTGTCGGC
 778▶ GlyGlnAlaValGlyThrValValLeuGlyAlaValGlyAlaLeuAlaLeuSerThrValSerGly

2395  ATCGCCTCGTTTATTGGCAACCCGTTCGGCCACGGGCTGCTGGTGCTGGTGCTCGCGGG
 799▶ IleAlaSerPheIleAlaAsnProPheGlyAlaLeuAlaThrGlyLeuLeuValLeuAlaGly

2458  CTGGTGGCCGTTTCCTGGGTACATTCCGCCTCCGCAGCAACCCATGAAGCG
 820▶ LeuValAlaAlaPheLeuAlaPheLeuAlaTyrArgTyrIleSerArgLeuArgSerAsnProMetLysAla

2521  CTGTACCCGATCACCACGCGCTCAAGGACGACCCCGGGCAACCGCCCGGGCGAG
 841▶ LeuTyrProIleThrThrArgAlaLeuLysAspAspProAlaArgGlyAlaThrAlaProGlyGlu

2584  GAAGAGGAGTTTGACCCGGCCAAACTGACGGCCAGCCGAGATGATCAAGTATATGTCG
 862▶ GluGluGluPheAspAlaAlaLysLeuGlnAlaArgGluMetIleLysTyrMetSer

2647  CTCGTGTCAGGCGGCGAGCGCAAGAGCAAGGCGAAAAGAGCAACAAGGGCCCCGCTG
 883▶ LeuValSerAlaValGluArgGlnHisLysAlaLysSerAsnLysGlyGlyProLeu

2710  CTGGCGACCCGGCTGACGCAGCTCCGCCTTCGGCGCGCCGGAGTACCAGCAGCTT
 904▶ LeuAlaThrArgLeuThrGlnLeuAlaLeuArgArgAlaProProGluTyrGlnGlnLeu

2773  CCGATGGCCGACGTCGGGGGCATGA
 925▶ ProMetAlaAspValGlyGlyAla•••
```

POLYNUCLEOTIDE VACCINE FORMULA IN PARTICULAR AGAINST BOVINE RESPIRATORY PATHOLOGY

This is a continuation-in-part of copending International Application PCT/FR97/01325 having an international filing date of Jul. 15, 1997, and designating the U.S. and claiming priority from French Application No. 96/09403, filed Jul. 19, 1996. Reference is also made to the concurrently filed applications of Audonnet et al.

The present invention relates to a vaccine formula allowing the vaccination of bovines in particular against respiratory pathology. It also relates to a corresponding method of vaccination.

All bovines are carriers of viruses and bacteria which are potentially pathogenic in widely variable degrees.

Viruses can multiply when the specific immunity is weakened and when there are lesions of the respiratory tract. They are then excreted by the animal and may then contaminate other animals.

Among the viruses which are encountered, there may be mentioned in particular the type 3 parainfluenza virus (PI-3), of moderate inherent pathogenicity, the bovine respiratory syncytial virus (RSV) and the bovine herpesvirus (BHV) also called infectious bovine rhinotracheitis (IBR) virus, of high inherent pathogenicities.

Another virus which is particularly important for its immunodepressant role and its harmful effects on reproduction is the mucosal disease virus or bovine pestivirus (BVDV).

These viruses generally manifest themselves by a primary phase of hyperthermia, flu syndrome and respiratory disorders, with digestive disorders (diarrhoeas) in the case of BVD. This phase may be accompanied by a secondary phase with the onset of bronchopneumonia linked to bacterial, in particular Pasteurella, infections which can lead to death. This phenomenon is exacerbated in particular by the immunodepression resulting from BVD infection or by the infection of macrophages by PI-3. Other symptoms may further appear, such as abortions with BVD and BHV.

It therefore appears necessary to try to develop an effective prevention against the principal viruses involved in bovine respiratory pathology.

Associations of vaccines against certain viruses responsible for bovine respiratory pathology have already been proposed in the past.

The associations developed so far were prepared from inactivated vaccines or live vaccines and, optionally, mixtures of such vaccines. Their development poses problems of compatibility between valencies and of stability. It is indeed necessary to ensure both the compatibility between the different vaccine valencies, whether from the point of view of the different antigens used or from the point of view of the formulations themselves, especially in the case where both inactivated vaccines and live vaccines are combined. The problem of the conservation of such combined vaccines and also of their safety especially in the presence of an adjuvant also exists. These vaccines are in general quite expensive.

Patent Applications WO-A-90 11092, WO-A-93 19183, WO-A-94 21797 and WO-A-95 20660 have made use of the recently developed technique of polynucleotide vaccines. It is known that these vaccines use a plasmid capable of expressing, in the host's cells, the antigen inserted into the plasmid. All the routes of administration have been proposed (intraperitoneal, intravenous, intramuscular, transcutaneous, intradermal, mucosal and the like). Various vaccination means can also be used, such as DNA deposited at the surface of gold particles and projected so as to penetrate into the animal's skin (Tang et al., Nature 356, 152–154, 1992) and liquid jet injectors which make it possible to transfect at the same time the skin, the muscle, the fatty tissues and the mammary tissues (Furth et al., Analytical Biochemistry, 205, 365–368, 1992). (See also U.S. Pat. Nos. 5,846,946, 5,620, 896, 5,643,578, 5,580,589, 5,589,466, 5,693,622, and 5,703, 055; Science, 259:1745–49, 1993; Robinson et al., seminars in IMMUNOLOGY, 9:271–83, 1997; Luke et al., J. Infect. Dis. 175(1):91–97, 1997; Norman et al., Vaccine, 15(8) :801–803, 1997; Bourne et al., The Journal of Infectious Disease, 173:800–7, 1996; and, note that generally a plasmid for a vaccine or immunological composition can comprise DNA encoding an antigen operatively linked to regulatory sequences which control expression or expression and secretion of the antigen from a host cell, e.g., a mammalian cell; for instance, from upstream to downstream, DNA for a promoter, DNA for a eukaryotic leader peptide for secretion, DNA for the antigen, and DNA encoding a terminator.

The polynucleotide vaccines may also use both naked DNAs and DNAs formulated, for example, inside cationic lipid liposomes.

G. J. M. COX has already proposed polynucleotide vaccination against type 1 bovine herpes virus in J. of Virology, Volume 67, No. 9, September 1993, 5664–5667. The authors have also described plasmids integrating the gI (gB), gIII (gC) and gIV (gD) genes.

In Vaccine, Volume 13, No. 4, 415–421, 1995, J. E. CROWE presents a general review of the different methods of vaccination against respiratory syncytial virus and against type 3 parainfluenza virus. This review reexamines all the possibilities offered by the current vaccination techniques and simply suggests that the polynucleotide immunization technique could be useful in the immunization strategy against RSV and PI-3. No plasmid construction or result of vaccination of bovines against these viruses is described in this document.

The invention therefore proposes to provide a multivalent vaccine formula which makes it possible to ensure vaccination against a number of pathogenic viruses involved in particular in bovine respiratory pathology and thus to ensure effective vaccination against this pathology.

Another objective of the invention is to provide such a vaccine formula combining different valencies while exhibiting all the criteria required for mutual compatibility and stability of the valencies.

Another objective of the invention is to provide such a vaccine formula which makes it possible to combine different jalencies in the same vehicle.

Another objective of the invention is to provide such a vaccine formula which is easy and inexpensive to use.

Yet another objective of the invention is to provide such a vaccine formula and a method for vaccinating bovines which makes it possible to obtain a multivalent protection with a high level of efficiency and of long duration, as well as good safety and an absence of residues.

The subject of the present invention is therefore a vaccine formula in particular against bovine respiratory pathology, comprising at least three polynucleotide vaccine valencies each comprising a plasmid integrating, so as to express it in vivo in the host cells, a gene with one bovine respiratory pathogen valency, these valencies being selected from the group consisting of bovine herpesvirus, bovine respiratory syncytial virus, mucosal disease virus and type 3 parainfluenza virus, the plasmids comprising, for each valency, one or more of the genes selected from the group consisting of gB and gD for the bovine herpesvirus, F and G for the bovine respiratory syncytial virus, E2, C+E1+E2 and E1+E2 for the mucosal disease virus, and HN and F for the type 3 parainfluenze virus.

Valency in the present invention is understood to mean at least one antigen providing protection against the virus for the pathogen considered, it being possible for the valency to contain, as subvalency, one or more modified or natural genes from one or more strains of the pathogen considered.

Pathogenic agent gene is understood to mean not only the complete gene but also the various nucleotide sequences, including fragments which retain the capacity to induce a protective response. The notion of a gene covers the nucleotide sequences equivalent to those described precisely in the examples, that is to say the sequences which are different but which encode the same protein. It also covers the nucleotide sequences of other strains of the pathogen considered, which provide cross-protection or a protection specific for a strain or for a strain group. It also covers the nucleotide sequences which have been modified in order to facilitate the in vivo expression by the host animal but encoding the same protein.

Preferably, the vaccine formula according to the invention comprises the four valences.

As regards the BHV valency, use is preferably made of the two genes encoding gB and gD, in different plasmids or in one and the same plasmid. Optionally, but less preferably, either of these genes can be used.

For the RSV valency, use is preferably made of the two G and F genes integrated into two different plasmids or into one and the same plasmid. Optionally, but less preferably, the F gene can be used alone.

For the BVD valency, use will preferably be made of a plasmid integrating the E2 gene. Optionally, but less preferably, a plasmid coding for E1 and E2 together or for the combination consisting of C, E1 and E2 can be used.

For the PI-3 valency, use is preferably made of the combination of the two HN and F genes in two different plasmids or in one and the same plasmid. It is also possible to use only the HN gene.

A preferred vaccine formula according to the invention comprises and ensures the expression of the BHV gB and gD genes, the RSV G and F genes, the BVD E2 genes and PI-3 HN and F genes.

The vaccine formula according to the invention can be provided in a dose volume of between 0.1 and 10 ml and in particular between 1 and 5 ml.

The dose will be generally between 10 ng and 1 mg, preferably between 100 ng and 50 μg and preferably between 1 μg and 250 μg per plasmid type.

Use will preferably be made of naked plasmids simply placed in the vaccination vehicle which will be in general physiological saline (0.9% NaCl), ultrapure water, TE buffer and the like. All the polynucleotide vaccine forms described in the prior art can of course be used.

Each plasmid comprises a promoter capable of ensuring the expression of the gene inserted, under its control, into the host cells. This will be in general a strong eukaryotic promoter and in particular a cytomegalovirus early CMV-IE promoter of human or murine origin, or optionally of another origin such as rats, pigs and guinea pigs.

More generally, the promoter may be either of viral origin or of cellular origin. As viral promoter other than CMV-IE, there may be mentioned the SV40 virus early or late promoter or the Rous sarcoma virus LTR promoter. It may also be a promoter from the virus from which the gene is derived, for example the gene's own promoter.

As cellular promoter, there may be mentioned the promoter of a cytoskeleton gene, such as for example the desmin promoter (Bolmont et al., Journal of Submicroscopic Cytology and Pathology, 1990, 22, 117–122; and Zhenlin et al., Gene, 1989, 78, 243–254), or alternatively the actin promoter.

When several genes are present in the same plasmid, these may be presented in the same transcription unit or in two different units.

The combination of the different vaccine valencies according to the invention may be preferably achieved by mixing the polynucleotide plasmids expressing the antigen (s) of each valency, but it is also possible to envisage causing antigens of several valencies to be expressed by the same plasmid.

The subject of the invention is also monovalent vaccine formulae comprising one or more plasmids encoding one or more genes from one of the viruses selected from the group consisting of BRSV, BVD and PI-3, the genes being those described above. Besides their monovalent character, these formulae may possess the characteristics stated above as regards the choice of the genes, their combinations, the composition of the plasmids, the dose volumes, the doses and the like.

The monovalent vaccine formulae may be used (i) for the preparation of a polyvalent vaccine formula as described above, (ii) individually against the actual pathology, (iii) combined with a vaccine of another type (live or inactivated whole, recombinant, subunit) against another pathology, or (iv) as booster for a vaccine as described below.

The subject of the present invention is in fact also the use of one or more plasmids according to the invention for the manufacture of a vaccine intended to vaccinate bovines first vaccinated by means of a first conventional vaccine of the type in the prior art, in particular, selected from the group consisting of a live whole vaccine, an inactivated whole vaccine, a subunit vaccine, a recombinant vaccine, this first vaccine having, that is to say containing or capable of expressing, the antigen(s) encoded by the plasmid(s) or antigen(s) providing cross-protection.

Remarkably, the polynucleotide vaccine has a potent booster effect which results in an amplification of the immune response and the acquisition of a long-lasting immunity.

In general, the first-vaccination vaccines can be selected from commercial vaccines available from various veterinary vaccine producers.

The subject of the invention is also a vaccination kit grouping together a first-vaccination vaccine as described above and a vaccine formula according to the invention for the booster. It also relates to a vaccine formula according to the invention accompanied by a leaflet indicating the use of this formula as a booster for a first vaccination as described above.

The subject of the present invention is also a method for vaccinating bovines against respiratory pathology, comprising the administration of the effective vaccine formula as described above. This vaccination method comprises the administration of one or more doses of the vaccine formula, it being possible for these doses to be administered in succession over a short period of time and/or in succession at widely spaced intervals.

The vaccine formulae according to the invention can be administered, in the context of this method of vaccination, by the different routes of administration proposed in the prior art for polynucleotide vaccination and by means of known techniques of administration.

The subject of the invention is also the method of vaccination consisting in making a first vaccination as described above and a booster with a vaccine formula according to the invention.

In a preferred embodiment of the process according to the invention, there is administered in a first instance, to the animal, an effective dose of the vaccine of the conventional, especially inactivated, live, attenuated or recombinant, type, or alternatively a subunit vaccine, so as to provide a first vaccination, and, within a period preferably of 2 to 6 weeks, the polyvalent or monovalent vaccine according to the invention is administered.

The invention also relates to the method of preparing the vaccine formulae, namely the preparation of the valencies and mixtures thereof, as evident from this description.

The invention will now be described in greater detail with the aid of the embodiments of the invention taken with reference to the accompanying drawings.

BRIEF DESCRIPTION OF THE DRAWINGS

FIG. No. 1: Plasmid pVR1012

FIG. No. 2: Sequence of the BHV-1 ST gB gene, SEQ ID NO:1

Figure 1:
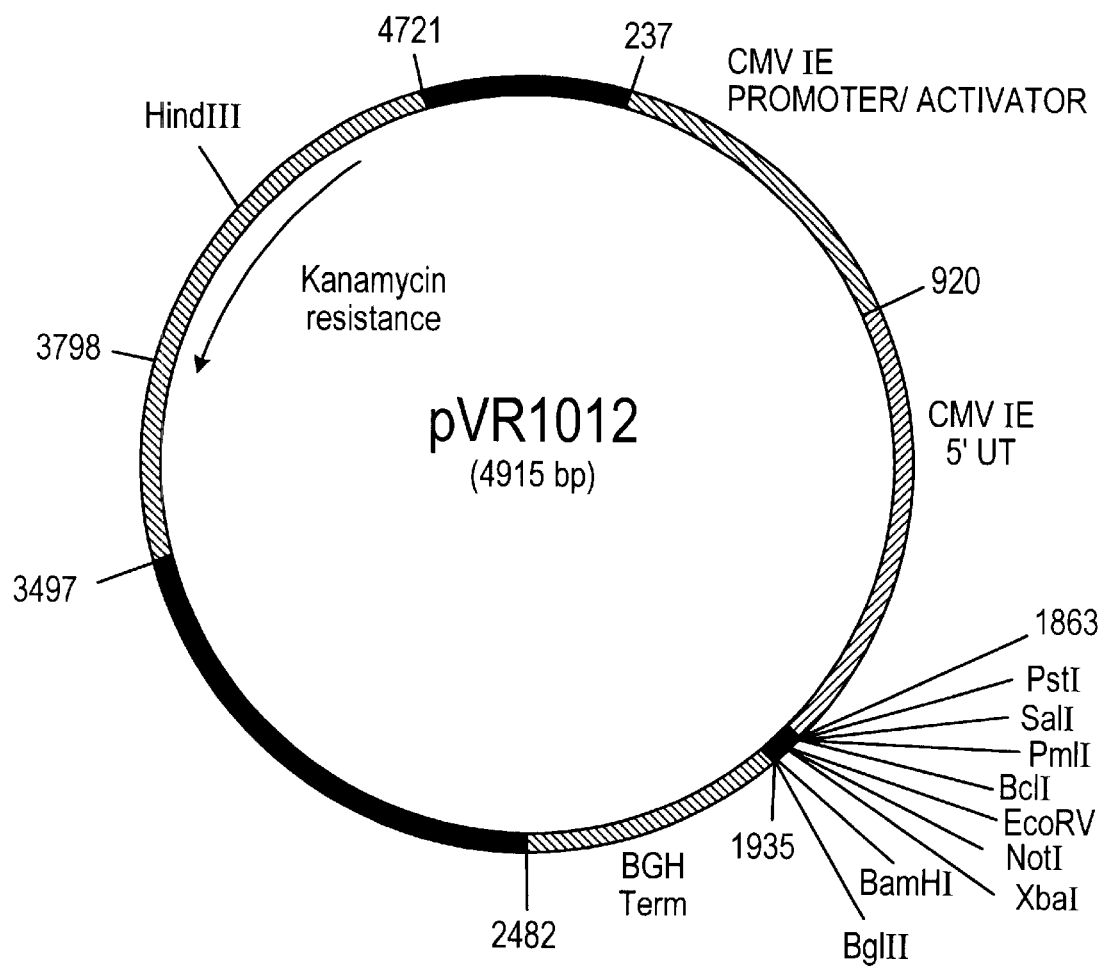
Figure 3:
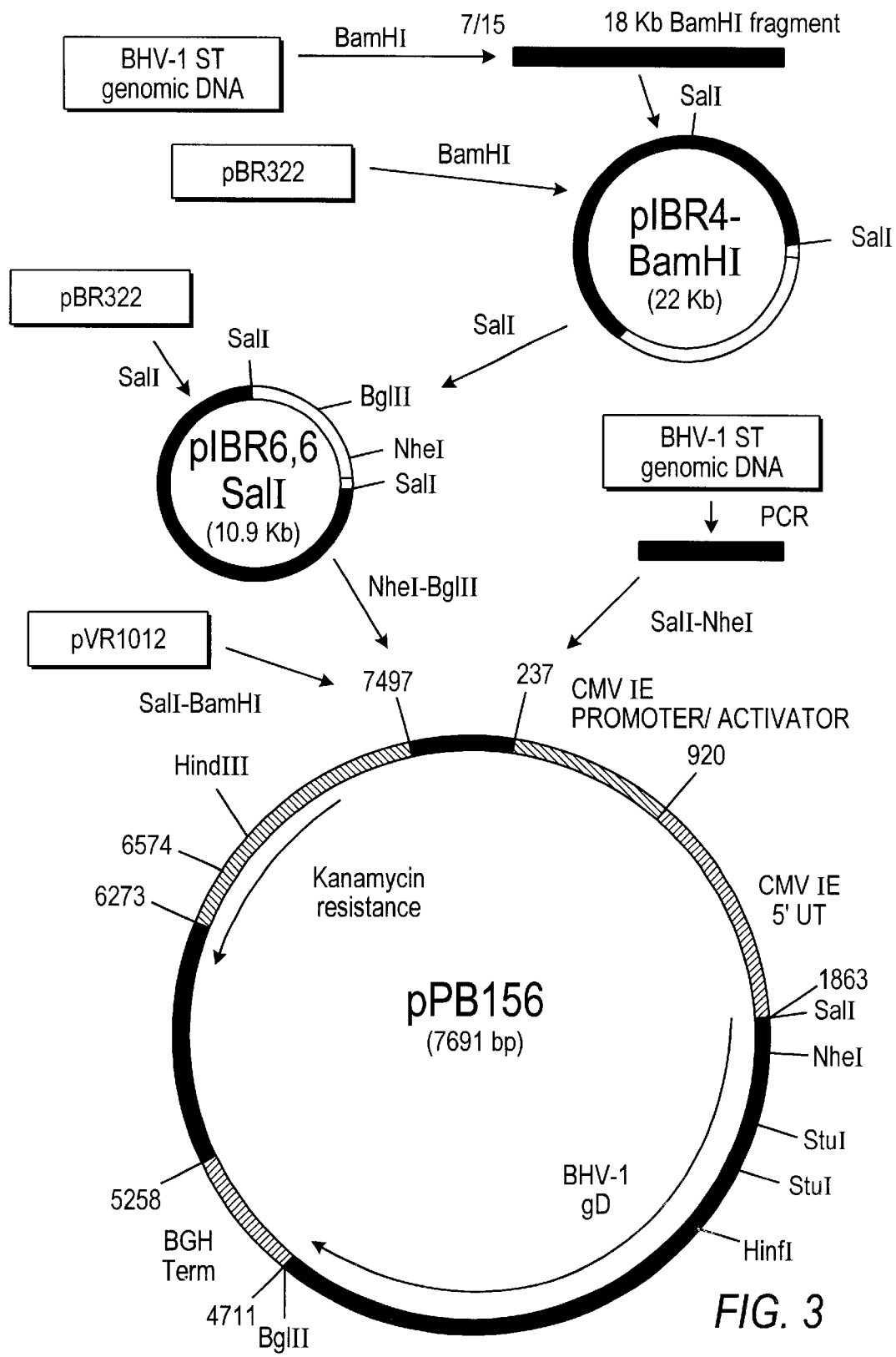
Figure 4:
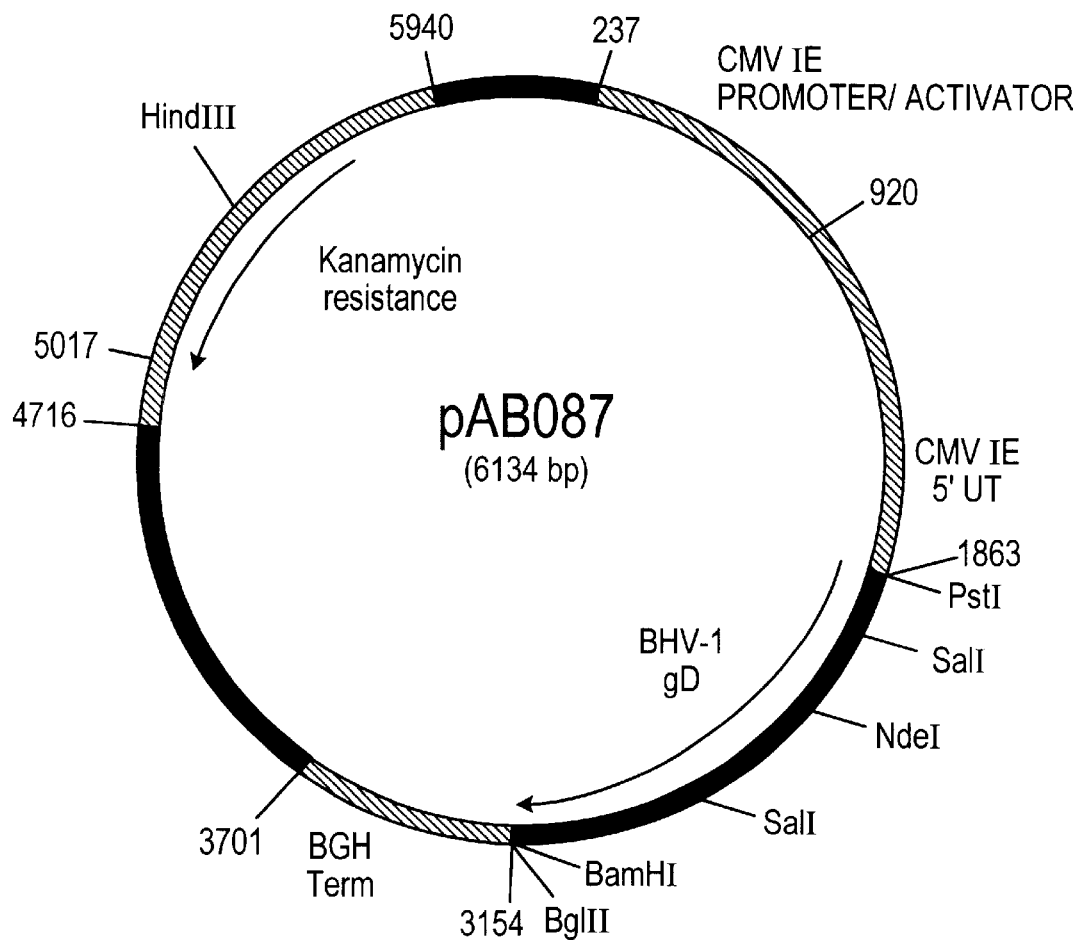
Figure 6:
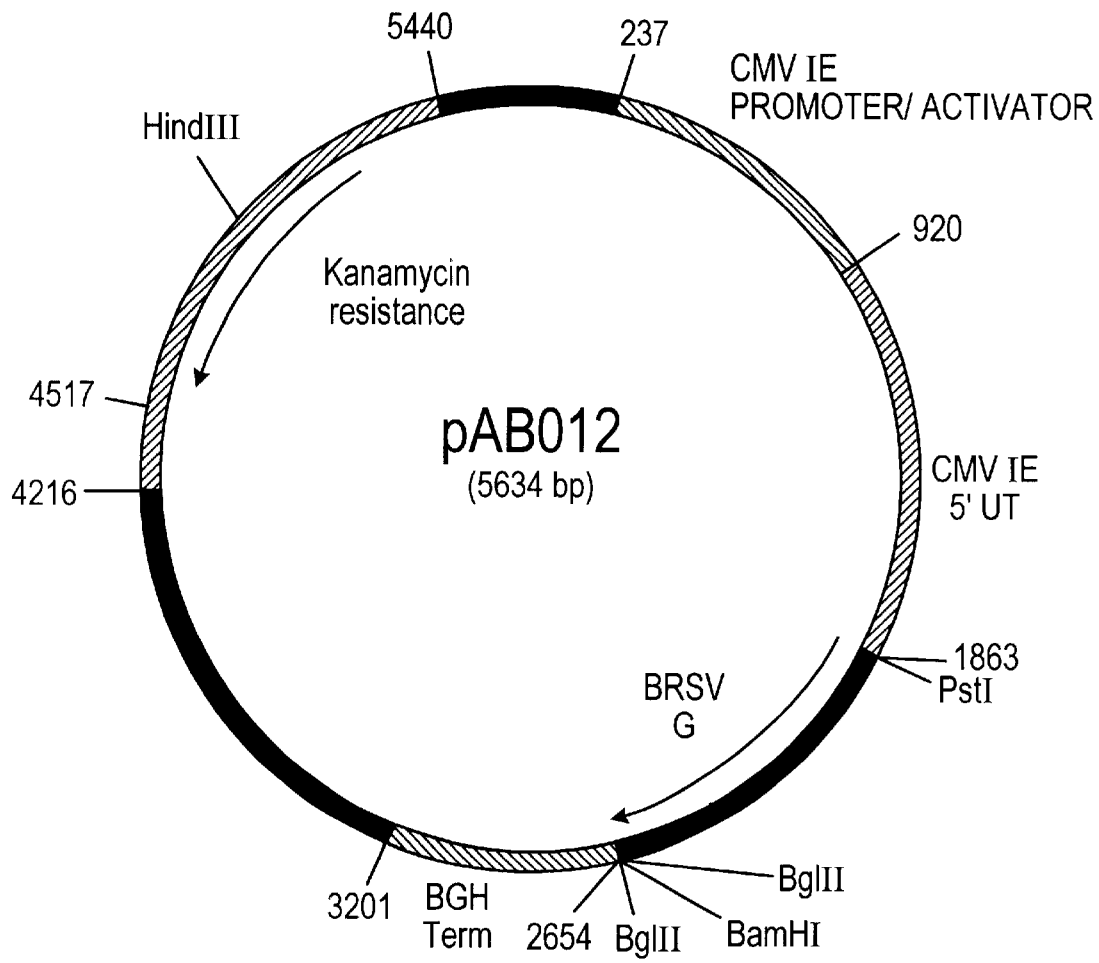
Figure 7:
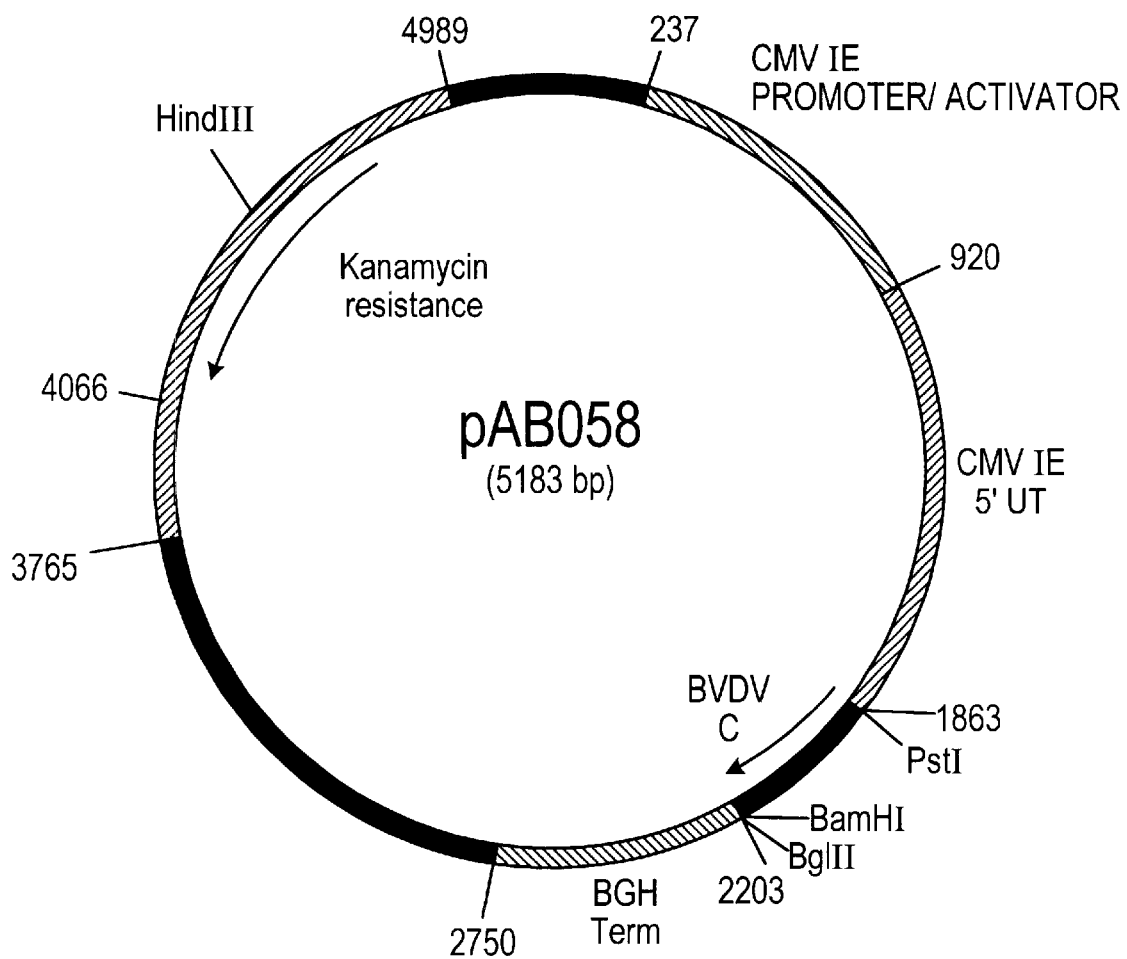
Figure 8:
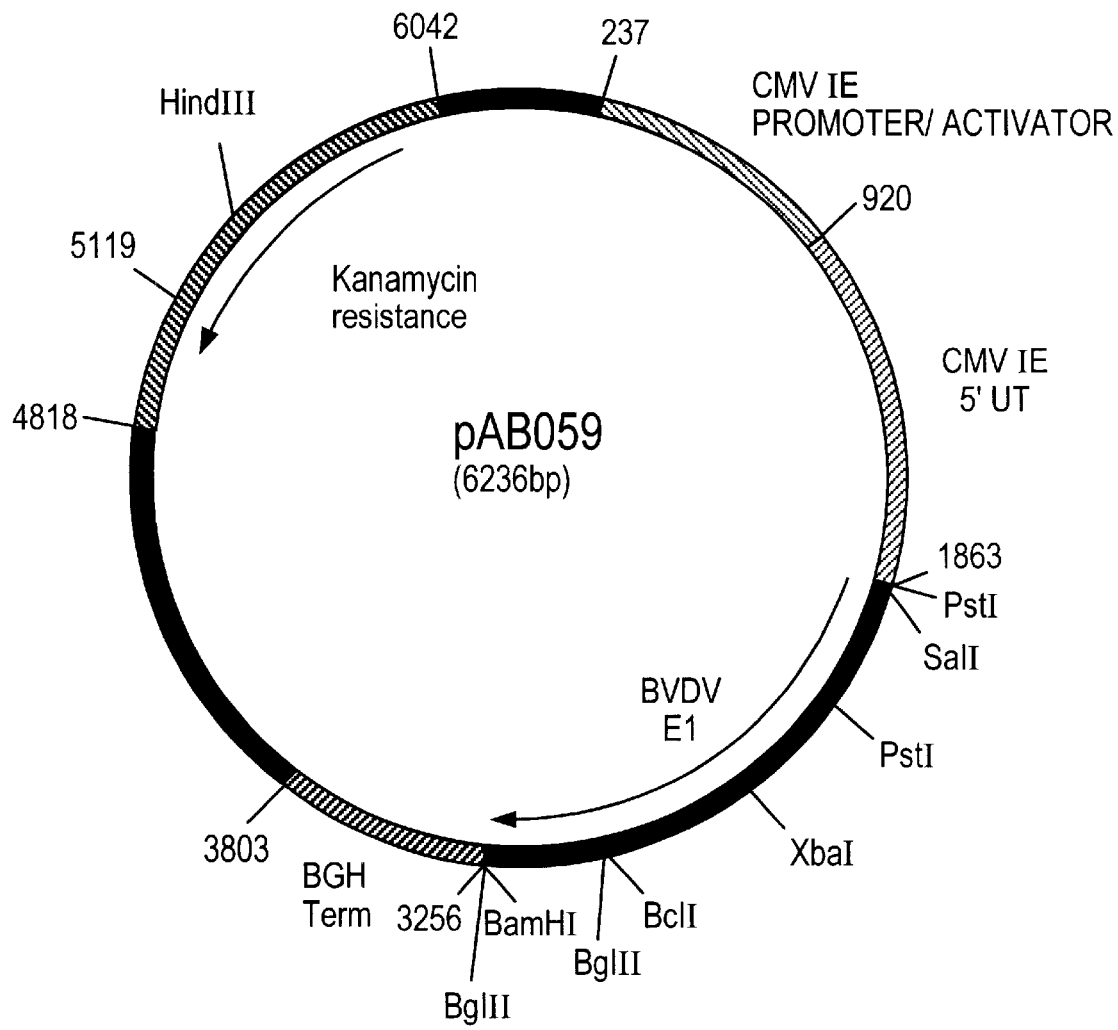
Figure 9:
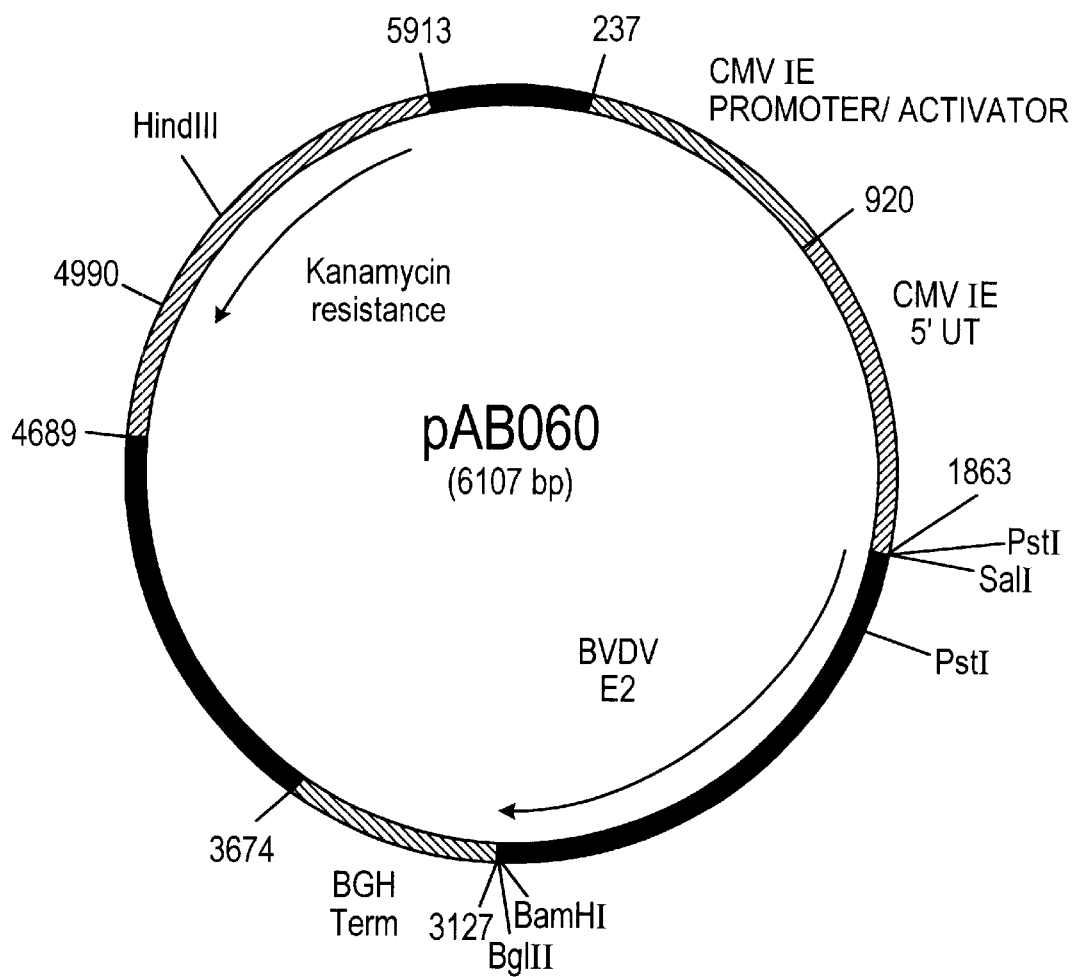
Figure 10:
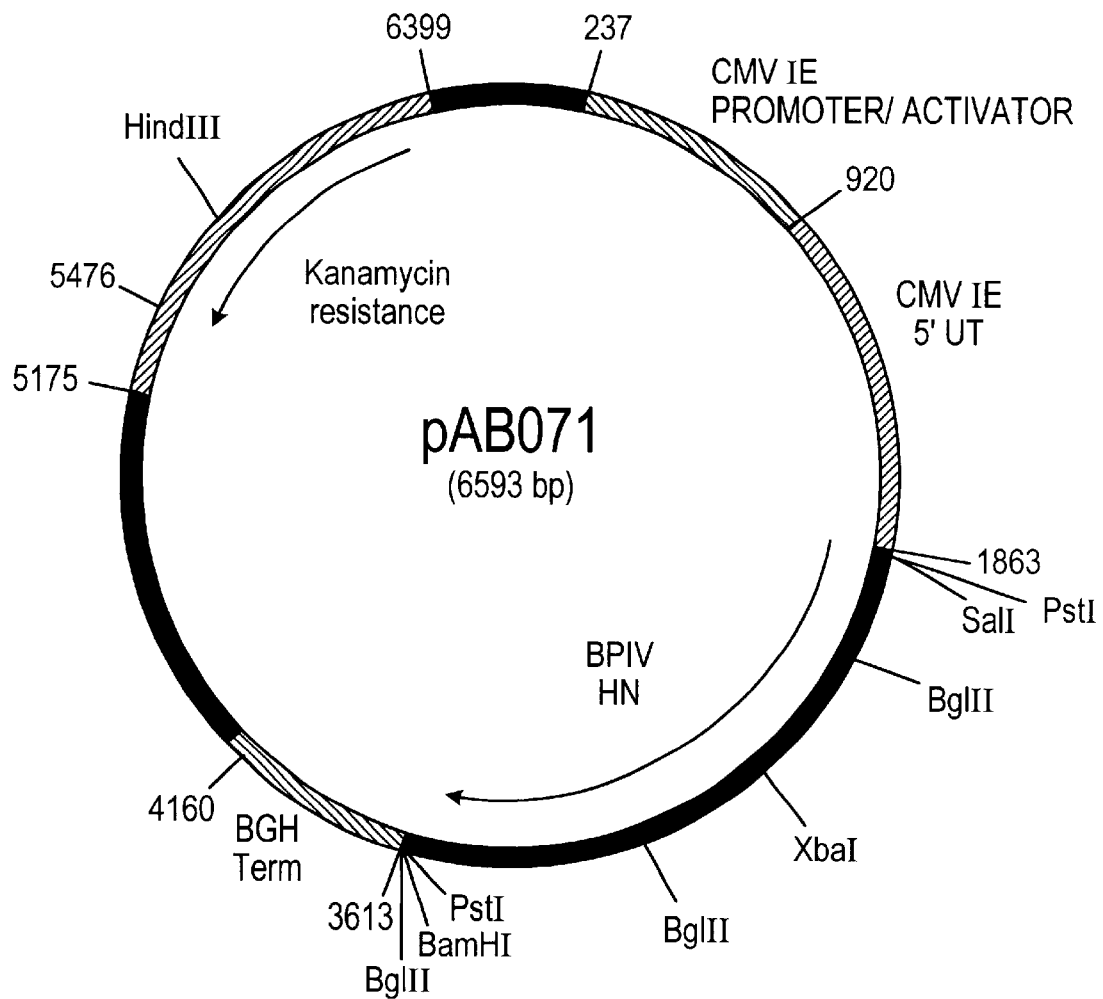
Figure 11:
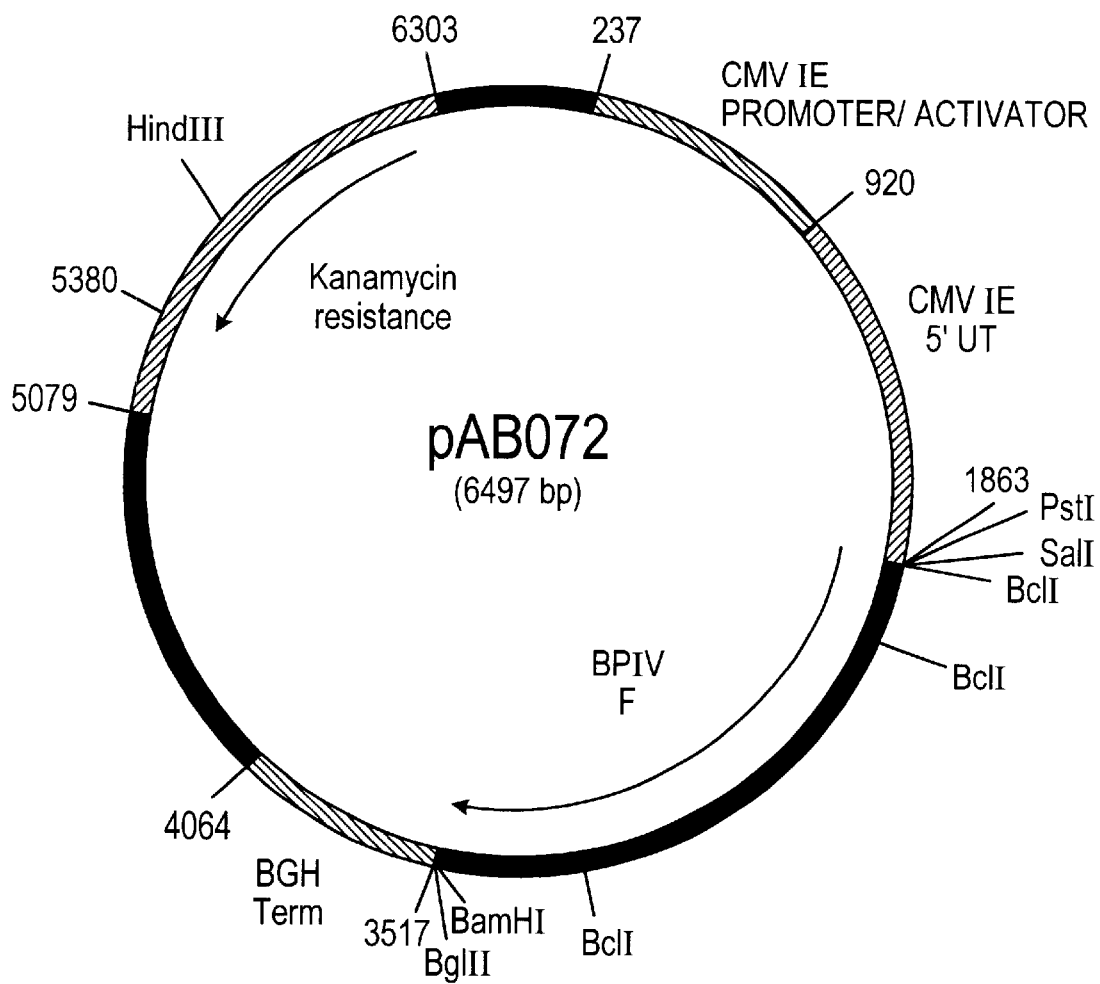

FIG. No. 3: Construction of the plasmid pPB156

FIG. No. 4: Plasmid pAB087

FIG. No. 5: Plasmid pAB011

FIG. No. 6: Plasmid pAB012

FIG. No. 7: Plasmid pAB058

FIG. No. 8: Plasmid pAB059

FIG. No. 9: Plasmid pAB060

FIG. No. 10: Plasmid pAB071

FIG. No. 11: Plasmid PAB072

SEQUENCE LISTING SEQUENCE ID NO

SEQ ID No. 1: Sequence of the BHV-1 gB gene (Strain ST)

SEQ ID No. 2: Oligonucleotide PB234

SEQ ID No. 3: Oligonucleotide PB235

SEQ ID No. 4: Oligonucleotide AB162

SEQ ID No. 5: Oligonucleotide AB163

SEQ ID No. 6: Oligonucleotide AB026

SEQ ID No. 7: Oligonucleotide AB027

SEQ ID No. 8: Oligonucleotide AB028

SEQ ID No. 9: Oligonucleotide AB029

SEQ ID No. 10: Oligonucleotide AB110

SEQ ID No. 11: Oligonucleotide AB111

SEQ ID No. 12: Oligonucleotide AB114

SEQ ID No. 13: Oligonucleotide AB115

SEQ ID No. 14: Oligonucleotide AB116

SEQ ID No. 15: Oligonucleotide AB117

SEQ ID No. 16: Oligonucleotide AB130

SEQ ID No. 17: Oligonucleotide AB131

SEQ ID No. 18: Oligonucleotide AB132

SEQ ID No. 19: Oligonucleotide AB133

EXAMPLES

Example 1
Culture of the Viruses

The viruses are cultured on the appropriate cellular system until a cytopathic effect is obtained. The cellular systems to be used for each virus are well known to persons skilled in the art. Briefly, the cells sensitive to the virus used, which are cultured in Eagle's minimum essential medium (MEM medium) or another appropriate medium, are inoculated with the viral strain studied using a multiplicity of infection of 1. The infected cells are then incubated at 37° C. for the time necessary for the appearance of a complete cytopathic effect (on average 36 hours).

Example 2
Extraction of the Viral Genomic DNAs

After culturing, the supernatant and the lysed cells are harvested and the entire viral suspension is centrifuged at 1000 g for 10 minutes at +4° C. so as to remove the cellular debris. The viral particles are then harvested by ultracentrifugation at 400,000 g for 1 hour at +4° C. The pellet is taken up in a minimum volume of buffer (10 mM Tris, 1 mM EDTA). This concentrated viral suspension is treated with proteinase K (100 μg/ml final) in the presence of sodium dodecyl sulphate (SDS) (0.5% final) for 2 hours at 37° C.. The viral DNA is then extracted with a phenol/chloroform mixture and then precipitated with 2 volumes of absolute ethanol. After leaving overnight at −20° C., the DNA is centrifuged at 10,000 g for 15 minutes at +4° C.. The DNA pellet is dried and then taken up in a minimum volume of sterile ultrapure water. It can then be digested with restriction enzymes.

Example 3
Isolation of the Viral Gemoric RNAs

The RNA viruses were purified according to techniques well known to persons skilled in the art. The genomic viral RNA of each virus was then isolated using the "guanidium thiocyanate/phenol-chloroform" extraction technique described by P. Chomczynski and N. Sacchi (Anal. Biochem., 1987, 162, 156–159).

Example 4
Molecular Biology Techniques

All the constructions of plasmids were carried out using the standard molecular biology techniques described by J. Sambrook et al. (*Molecular Cloning: A Laboratory Manual*, 2nd Edition, Cold Spring Harbor Laboratory, Cold Spring Harbor, N.Y., 1989). All the restriction fragments used for the present invention were isolated using the "Geneclean" kit (BIO 101 Inc. La Jolla, Calif.).

Example 5
RT-PCR Technique

Specific oligonucleotides (comprising restriction sites at their 5' ends to facilitate the cloning of the amplified fragments) were synthesized such that they completely cover the coding regions of the genes which are to be amplified (see specific examples). The reverse transcription (RT) reaction and the polymerase chain reaction (PCR) were carried out according to standard techniques (J. Sambrook et al., *Molecular Cloning: A Laboratory Manual*, 2nd Edition, Cold Spring Harbor Laboratory, Cold Spring Harbor, N.Y., 1989). Each RT-PCR reaction was performed with a pair of specific amplimers and taking, as template, the viral genomic RNA extracted. The complementary DNA amplified was extracted with phenol/chloroform/isoamyl alcohol (25:24:1) before being digested with restriction enzymes.

Example 6
Plasmid pVR1012

The plasmid pVR1012 (FIG. No. 1) was obtained from Vical Inc., San Diego, Calif., USA. Its construction has been described in J. Hartikka et al. (Human Gene Therapy, 1996, 7, 1205–1217).

Example 7
Construction of the Plasmid pPB156 (BHV-1 gB Gene)

The BVH-1 bovine herpesvirus (ST strain) genomic DNA (Leung-Tack P. et al. Virology, 1994, 199, 409–421) was prepared according to the technique described in Example 2 and was digested with BamHI. After purification, the 18 kbp BamHI-BamHI fragment was cloned into the vector pBR322, previously digested with BamHl, to give the plasmid pIBR-4-BamHI (22 kbp).

The plasmid pIBR-4-BamHI was then digested with SalI in order to liberate a 6.6 kbp SalI-SalI fragment containing the gene encoding the BHV-1 gB glycoprotein (FIG. No. 2 and SEQ ID No. 1). This fragment was cloned into the vector pBR322, previously digested with SalI, to give the plasmid pIBR-6,6-SalI (10.9 kbp).

The plasmid pIBR-6,6-SalI was digested with NheI and BglII in order to liberate a 2676 bp NheI-BglII fragment containing the gene encoding the bovine herpesvirus (BHV-1) gB glycoprotein (fragment A).

A PCR reaction was carried out with the genomic DNA from the bovine herpesvirus (BHV-1) (ST strain) and with the following oligonucleotides:

PB234 (30 mer) (SEQ ID No. 2) 5' TTGTCGACATGGC-CGCTCGCGGCGGTGCTC 3'

PB235 (21 mer) (SEQ ID No. 3) 5' GCAGGGCAGCG-GCTAGCGCGG 3' so as to isolate the 5' part of the gene encoding the BHV-1 gB glycoprotein. After purification, the 153 bp PCR product was digested with SalI and NheI in order to isolate a 145 bp SalI-NheI fragment (fragment B).

The fragments A and B were ligated together with the vector pVR1012 (Example 6), previously digested with SalI and BamHI, to give the plasmid pPB156 (7691 bp) (FIG. No. 3).

Example 8
Construction of the Plasmid pAB087 (BHV-1 gD Gene)

A PCR reaction was carried out with the genomic DNA from the bovine herpesvirus (BHV-1) (ST strain) (P. Leung-Tack et al., Virology, 1994, 199, 409–421), prepared according to the technique described in Example 2, and with the following oligonucleotides:

AB162 (31 mer) (SEQ ID No. 4) 5' AAACTGCAGATG-CAAGGGCCGACATTGGCCG 3'

AB163 (30 mer) (SEQ ID No. 5) 5' ATCTTGTACCATAT-GACCGTGGCGTTG 3' so as to amplify the 5' part of the gene encoding the bovine herpesvirus (BHV-1) gD glycoprotein (GenBank sequence accession No.=L26360) in the form of a 338 bp PCR fragment. After purification, this fragment was digested with PstI and NdeI in order to isolate a 317 bp PstI-NdeI fragment (fragment A).

The plasmid pBHV001 (P. Leung-Tack et al., Virology, 1994, 199, 409–421) was digested with NdeI and StyI in order to liberate a 942 bp fragment containing the 3' part of the gene encoding the BHV-1 gD glycoprotein (fragment B).

The fragments A and B were ligated together with the vector pVR1012 (Example 6), previously digested with PstI and XbaI, to give the plasmid pAB087 (6134 bp) (FIG. No. 4).

Example 9
Construction of the Plasmid pAB0111 (BRSV F Gene)

An RT-PCR reaction according to the technique described in Example 5 was carried out with the genomic RNA from the bovine respiratory syncytial virus (BRSV) (391–2 strain) (R. Lerch et al., J. Virology, 1991, 181, 118–131), prepared as indicated in Example 3, and with the following oligonuclebtides:

AB026 (33 mer) (SEQ ID No. 6) 5' AAAACTGCAGG-GATGGCGGCAACAGCCATGAGG 3'

AB027 (31 mer) (SEQ ID No. 7) 5' GCGGATCCTCATT-TACTAAAGGAAAGATTG 3' so as to isolate the gene encoding the F fusion glyco-protein (BRSV F) in the form of a 1734 bp PCR fragment. After purification, this fragment was digested with PstI and BamHI in order to isolate a 1715 bp PstI-BamHI fragment. This fragment was ligated with the vector pVR1012 (Example 6), previously digested with PstI and BamHI, to give the plasmid pAB011 (6587 bp) (FIG. No. 5).

Example 10
Construction of the Plasmid pAB012 (BRSV G Gene)

An RT-PCR reaction according to the technique described in Example 5 was carried out with the genomic RNA from the bovine respiratory syncytial virus (BRSV) (391–2 strain) (R. Lerch et al., J. Virology, 1991, 64, 5559–5569) and with the following oligonucleotides:

AB028 (32 mer) (SEQ ID No. 8) 5' AAAACTGCAGAT-GTCCAACCATACCCATCATC 3'

AB029 (35 mer) (SEQ ID No. 9) 5° CGCGGATCCCTA-GATCTGTGTAGTTGATTGATTTG 3' so as to isolate the gene encoding the G protein (BRSV G) in the fomn of a 780 bp PCR fragment. After purification, this fragment was digested with PstI and BamHI in order to isolate a 763 bp PstI-BamHI fragment. This fragment was ligated with the vector pVR1012 (Example 6), previously digested with PstI and BamHI, to give the plasma pAB012 (5634 bp) (FIG. No. 6).

Example 11
Construction of the Plasmid pABOS8 (BVDV C Gene)

An RT-PCR reaction according to the technique described in Example 5 was carried out with the genomic RNA from the bovine viral diarrhoea virus (BVDV) (Osloss strain) (L. De Moerlooze et al., J. Gen. Virol., 1993, 74, 1433–1438), prepared according to the technique described in Example 3, and with the following oligonucleotides:

AB110 (35 mer) (SEQ ID No. 10) 5' AAAACTGCAGAT-GTCCGACACAAAAGCAGAAGGGG 3'

AB111 (47 mer) (SEQ ID No. 11) 5' GCGGATCCT-CAATAAAAATCATTCCCACTGCGACT-TGAAACAAAAC 3' so as to amplify a 342 bp fragment containing the gene encoding the C capside protein from the BVDV virus. After purification, the RT-PCR product was digested with PstI and BamHI to give a 324 bp PstI-BamHI fragment.

This fragment was ligated with the vector pVR1012 (Example 6), previously digested with PstI and BamHI, to give the plasmid pAB058 (5183 bp) (FIG. No. 7).

Example 12
Construction of the Plasmid pAB059 (BVDV E1 "Gene")

An RT-PCR reaction according to the technique described in Example 5 was carried out with the genomic RNA from the bovine viral diarrhoea virus (BVDV) (Osloss strain) (L. De Moerlooze et al., J. Gen. Virol., 1993, 74, 1433–1438) and with the following oligonucleotides:

AB114 (32 mer) (SEQ ID No. 12) 5' ACGCGTCGACAT-GAAGAAACTAGAGAAAGCCC 3'

AB115 (33 mer) (SEQ ID No. 13) 5' GCGGGATCCT-CAGCCGGGTTTGCAAACTGGGAG 3' so as to isolate the sequence encoding the BVDV virus E1 protein in the form of a 1381 bp PCR fragment. After purification, this fragment was digested with SalI and BamHI to give a 1367 bp SalI-BamHI fragment.

This fragment was ligated with the vector pVR1012 (Example 6), previously digested with SalI and BamHI, to give the plasmid pAB059 (6236 bp) (FIG. No. 8).

Example 13
Construction of the Plasmd pAB060 (BVDV E2 "Gene")

An RT-PCR reaction according to the technique described in Example 5 was carried out with the genomic RNA from the bovine viral diarrhoea virus (BVDV) (Osloss strain) (L. De Moerlooze et al., J. Gen. Virol., 1993, 74, 1433–1438) and with the following oligonucleotides:

AB116 (36 mer) (SEQ ID No. 14) 5' ACGCGTCGACAT-GACGACTACTGCATTCCTGGTATG 3'

AB116 (33 mer) (SEQ ID No. 15) 5° C.GCGGATCCTCAT-TGACGTCCCGAGGTCATTTG 3' so as to isolate the sequence encoding the BVDV virus E2 protein in the form of a 1252 bp PCR fragment. After purification, this fragment was digested with SalI and BamHI to give a 1238 bp SalI-BamHI fragment.

This fragment was ligated with the vector pVR1012 (Example 6), previously digested with SalI and BamHI, to give the plasmid pAB060 (6107 bp) (FIG. No. 9).

Example 14
Construction of the Plasmid pAB071 (BPIV HN Gene)

An RT-PCR reaction according to the technique described in Example 5 was carried out with the genomic RNA from the type 3 bovine parainfluenza virus (PI3=BPIV) and with the following oligonucleotides:

AB130 (33 mer) (SEQ ID No. 16) 5' TTTGTCGACATG-GAATATTGGAAACACACAAAC 3'

AB131 (33 mer). (SEQ ID No. 17) 5' TTTGGATCCT-TAGCTGCAGTTTTTCGGAACTTC 3' so as to isolate the gene encoding the BPIV HN glycoprotein (HN gene sequence deposited by H. Shibuta in 1987. GenBank sequence accession No.=Y00115) in the form of a 1737 bp PCR fragment. After purification, this fragment was digested with SalI and BamHI in order to isolate a 1725 bp SalI-BamHI fragment. This fragment was ligated with the vector pVR1012 (Example 6), previously digested with SalI and BamHI, to give the plasmid pAB071 (6593 bp) (FIG. No. 10).

Example 15
Construction of the Plasmid pAB072 (BPIV F Gene)

An RT-PCR reaction according to the technique described in Example 5 was carried out with the genomic RNA from the type 3 bovine parainfluenza virus (PI3=BPIV) and with the following oligonucleotides:

AB132 (30 mer) (SEQ ID No. 18) 5' TTTGTCGACATGAT-CATCACAAACACAATC 3'

AB133 (30 mer) (SEQ ID No. 19) 5' TTTGGATCCTCAT-TGTCTACTTGTTAGTAC 3' so as to isolate the gene encoding the BPIV F glyco-protein (F gene sequence deposited by H. Shibuta in 1987. GenBank sequence accession No.=Y00115) in the form of a 1641 bp PCR fragment. After purification, this fragment was digested with SalI and BamHI in order to isolate a 1629 bp SalI-BamHI fragment. This fragment was ligated with the vector pVR1012 (Example 6), previously digested with SalI and BamHI, to give the plasmid pAB072 (6497 bp) (FIG. No. 11).

Example 16
Preparation and Purification of the Plasmids

For the preparation of the plasmids intended for the vaccination of animals, any technique may be used which makes it possible to obtain a suspension of purified plasmids predominantly in a supercoiled form. These techniques are well known to persons skilled in the art. There may be mentioned in particular the alkaline lysis technique followed by two successive ultracentrifugations on a caesium chloride gradient in the presence of ethidium bromide as described in J. Sambrook et al. (*Molecular Cloning: A Laboratory Manual,* 2nd edition, Cold Spring Harbor Laboratory, Cold Spring Harbor, N.Y., 1989). Reference may also be made to Patent Applications PCT WO 95/21250 and PCT WO 96/02658, which describe methods for producing, on an industrial scale, plasmids which can be used for vaccination. For the purposes of the manufacture of vaccines (see Example 17), the purified plasmids are resuspended so as to obtain solutions at a high concentration (>2 mg/ml) which are compatible with storage. To do this the plasmids are resuspended either in ultrapure water or in TE buffer (10 mM Tris-HCl; 1 mM EDTA, pH 8.0).

Example 17
Manufacture of the Associated Vaccines

The various plasmids necessary for the manufacture of an associated vaccine are mixed starting with their concentrated solutions (Example 16). The mixtures are prepared such that the final concentration of each plasmid corresponds. to the effective dose of each plasmid. The solutions which can be used to adjust the final concentration of the vaccine may be either a 0.9% NaCl solution, or PBS buffer.

Specific formulations such as liposomes or cationic lipids, may also be used for the manufacture of the vaccines.

Example 18
Vaccination of Bovines

The bovines are vaccinated with doses of 100 μg, 250 μg or 500 μg per plasmid. The injections are performed with a needle by the intramuscular route either at the level of the gluteus muscle, or at the level of the neck muscles. The vaccinal doses are administered in volumes of between 1 and 5 ml.

---

What is claimed is:

1. An immunogenic composition for inducing in a bovine host an immunoloqlcal response against bovine respiratory syncytial virus comprising at least one plasmid that contains and expresses in vivo in a bovine host cell nucleic acid molecule(s) having sequence(s) encoding bovine respiratory syncytial virus F protein, or G protein, or F and G proteins.

2. The immunogenic composition according to claim 1 which comprises a plasmid that contains and expresses in vivo in a bovine host cell nucleic acid molecule(s) having sequence(s) encoding bovine respiratory syncytial virus F and G proteins.

3. The immunogenic composition according to claim 1 which comprises a first plasmid that contains and expresses in vivo in a bovine host cell a nucleic acid molecule having a sequence encoding bovine respiratory syncytial virus F protein; and a second plasmid that contains and expresses in vivo in a bovine host cell a nucleic acid molecule having a sequence encoding bovine respiratory syncytial virus G protein.

4. The immunogenic composition according to claim 1 which comprises a plasmid that contains and expresses in vivo in a bovine host cell a nucleic acid molecule having a sequence encoding bovine respiratory syncytial virus F protein.

5. A vaccine composition against bovine respiratory syncytial virus comprising at least one plasmid that contains and expresses in vivo in a bovine host cell nucleic acid molecule (s) having sequence(s) encoding bovine respiratory syncytial virus F protein, or G protein or F and G proteins.

6. The vaccine composition according to claim 5 which comprises a plasmid that contains and expresses in vivo in a bovine host cell nucleic acid molecule(s) having sequence (s) encoding bovine respiratory syncytial virus F and G proteins.

7. The vaccine composition according to claim 5 which comprises a first plasmid that contains and expresses in vivo in a bovine host cell a nucleic acid molecule having a sequence encoding bovine respiratory syncytial virus F protein; and a second plasmid that contains and expresses in vivo in a bovine host cell a nucleic acid molecule having a sequence encoding bovine respiratory syncytial virus G protein.

8. The vaccine composition according to claim 5 which comprises a plasmid that contains and expresses in vivo in a bovine host cell a nucleic acid molecule having a sequence encoding bovine respiratory syncytial virus F protein.

9. A method for inducing an immunological response in a bovine comprising: administering to said bovine a vaccine selected from the group consisting of a live whole vaccine, an inactivated whole vaccine, a subunit vaccine, and a recombinant vaccine; and thereafter, administering to said bovine an immunogenic or vaccine composition as claimed in any one of claims 1–4 or 5–8.

10. A method for inducing an immunological response in a bovine comprising administering said bovine an immunogenic or vaccine composition as claimed in any one of claims 1–4 or 5–8.

11. A kit comprising (i) an immunogenic or vaccine composition according to any one of claims 1–4 or 5–8, and (ii) a bovine vaccine selected from the group consisting of a live whole vaccine, an inactivated whole vaccine, a subunit vaccine, and recombinant vaccine.

12. A method of vaccinating a bovine comprising: administering to said bovine a vaccine selected from the group consisting of a live whole vaccine, an inactivated whole vaccine, a subunit vaccine, and a recombinant vaccine; and thereafter, administering to said bovine an immunogenic or vaccine composition as claimed in any one of claims 1–4 or 5–8.

13. A method of vaccinating a bovine comprising administering to said bovine an immunogenic or vaccine composition as claimed in any one of claims 1–4 or 5–8.

* * * * *

UNITED STATES PATENT AND TRADEMARK OFFICE
CERTIFICATE OF CORRECTION

PATENT NO. : 6,376,473 B1  Page 1 of 1
DATED : April 23, 2002
INVENTOR(S) : Jean-Christophe Audonnet et al.

It is certified that error appears in the above-identified patent and that said Letters Patent is hereby corrected as shown below:

<u>Title page,</u>
Item [75], Inventors: change "Lyons" to -- Lyon --.
Item [73], Assignee: change "Lyons" to -- Lyon --

<u>Column 8,</u>
Line 20, change "5²" to -- 5' --.

<u>Column 9,</u>
Line 10, change "5²" to -- 5' --.

Signed and Sealed this

Sixteenth Day of July, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.   : 6,376,473 B1
DATED        : January 15, 1999
INVENTOR(S)  : Jean-Christophe Audonnet et al.

It is certified that error appears in the above-identified patent and that said Letters Patent is hereby corrected as shown below:

Column 1,
Line 10, insert:
-- Serial Nos. 09/232,278, 09/232,468, 09/232,497 and 09/232,478 and the concurrently filed application of Rijsewijk et al., Serial No. 09/232,469. All of the above-mentioned applications, as well as documents cited herein and documents referenced or cited in documents cited herein, are hereby incorporated herein by reference. Vectors of vaccines or immunological compositions of the aforementioned applications, as well as of documents cited herein or documents referenced or cited in documents herein or portions of such vectors (e.g., one or more or all of regulatory sequences such as for promoter, leader for secretion, termination), may to the extent practicable with respect to the preferred host of this application, also be employed in the practice of this invention; and, DNA for vectors of vaccines or immunological compositions herein can be obtained from available sources and knowledge in the art, e.g., GeneBank, such that from this disclosure, no under experimentation is required to make or use such vectors. --

Signed and Sealed this

Fourth Day of November, 2003

JAMES E. ROGAN
*Director of the United States Patent and Trademark Office*

SEQUENCE LISTING

<160> NUMBER OF SEQ ID NOS: 19

<210> SEQ ID NO 1
<211> LENGTH: 2799
<212> TYPE: DNA
<213> ORGANISM: Bovine herpesvirus 2

<400> SEQUENCE: 1
atggccgctc gcggcggtgc tgaacgcgcc gcgggcgccg gagacggtcg g cgaggacag    60

-continued

| | |
|---|---|
| cgtcgtcatc tacgaccggg acgtgttctc gctgctctac gcggtcctgc a gcgcctggc | 120 |
| gccggcgggg cgcgcgccgc gctagccgct gccctgctat gggcgacgtg g gccctgctg | 180 |
| ctggcggcgc ccgccgcggg gcgaccggcg acaacgcccc cggcgccccc g cccgaagag | 240 |
| gccgcgagcc cggcgccccc cgcgagcccc agccccccg gccccgacgg c gacgacgcc | 300 |
| gccagccccg acaacagcac ggacgtgcgc gccgcgctcc ggctcgcgca g gcggccggg | 360 |
| gaaaactcgc gcttcttcgt gtgcccgccg ccctcgggcg ccacggtggt c cggctcgcg | 420 |
| cccgcgcggc cgtgccccga gtacgggctc gggcggaact acacggaggg c atcggcgtc | 480 |
| atttacaagg agaacatcgc gccgtacacg ttcaaggcct acatttacaa a aacgtgatc | 540 |
| gtgaccacga cctgggcggg cagcacgtac gcggccatta caaaccagta c acggaccgc | 600 |
| gtgcccgtgg gcatgggcga gatcacggac ctggtggaca agaagtggcg c tgcctttcg | 660 |
| aaagccgagt acctgcgcag cgggcgcaag gtggtggcct ttgaccgcga c gacgacccc | 720 |
| tgggaggcgc cgctgaagcc cgcgcggctg agcgcgcccg gggtgcgggg c tggcacacg | 780 |
| acggacgatg tgtacacggc gctgggctcg gcggggctct accgcacggg c acctctgtg | 840 |
| aactgcatcg tggaagaagt ggaggcgcgc tcggtgtacc cgtacgactc g ttcgcgctc | 900 |
| tcgaccgggg acattatcta catgtcgccc ttttacgggc tgcgcgaggg c gcgcaccgc | 960 |
| gagcacacca ggctactcgc cggagcgctt ccagcagatc gagggctact a caagcgcga | 1020 |
| catggccacg ggccggcgcc tcaaggagcc ggtctcgcgg aacttttgc g tacacagca | 1080 |
| cgtgacggta gcctgggact gggtgcccaa gcgcaaaaac gtgtgctcgc t tggccaagtg | 1140 |
| gcgcgaggcg gacgaaatgc tgcgagacga gagccgcggg aacttccgct t cacggcccg | 1200 |
| ctcgctctcg gcgacctttg tgagcgacag ccacaccttc gcgttgcaga a tgtgccgct | 1260 |
| gagcgactgc gtgatcgaag aggccgaggc cgcggtcgag cgcgtctacc g cgagcgcca | 1320 |
| caacggcacg cacgtgctgt cgggcagcct ggagacgtac ctggcgcgcg g cggctttgt | 1380 |
| cgtggccttc cggcgatgct cagcaacgag ctggccaagc tgtacctgca g gagctggcg | 1440 |
| cgctcgaacg gcacgctcga ggggctgttc ccgccgcgg cgcccaagcc g ggcccgcgg | 1500 |
| cgcgcgcgcc gcgccgcgcc gtccgcgccc ggcagcccgg gcgcggccaa c gggcccgcc | 1560 |
| ggcgacggcc acgccggcgg gcgggtgact accgtgagct cggccgagtt t gcggcgctg | 1620 |
| cagttcacct acgaccacat ccaggaccac gtgaacacca tgttcagccg c ctggccacg | 1680 |
| tcctggtgcc tgctgcagaa caaggagcgc gccctgtggg ccgaggcggc t aagctcaac | 1740 |
| cccagcgcgg cggccagcgc tgcgctggac cgccgcgcc ccgcgcgcat g ttgggggac | 1800 |
| gccatggccg tgacgtactg ccacgagctg gcgaggggc gcgtgttcat c gagaactcg | 1860 |
| atgcgcgcgc ccggcggcgt ttgctacagc cgcccgccgg tctcctttgc c ttcggcaac | 1920 |
| gagagcgagc cggtggaggg ccagctcggc gaggacaacg agctgctgcc g ggccgcgag | 1980 |
| ctcgtggagc cctgcaccgc caaccacaag cgctacttcc gctttggcgc g gactacgtg | 2040 |
| tactacgaga actacgcgta cgtgcggcgg gtcccgctcg cggagctgga g gtgatcagc | 2100 |
| acctttgtgg acctaaacct cacggttctg gaggaccgcg agttcttgcc g ctagaagtg | 2160 |
| tacacgcgcg ccgagctcgc cgacacgggt ctgctcgact acagcgagat a cagcgccgc | 2220 |
| aaccagctgc acgagctccg gttctacgac attgaccgcg tggtcaagac g gacggcaat | 2280 |
| atggccatca tgcagggct cgccaacttc tttcagggcc tgggcgccgt c gggcaggcg | 2340 |
| gtgggcacgg tggtgctggg cgccgcgggt gccgcgctct cgaccgtgtc g ggcatcgcc | 2400 |
| tcgtttattg cgaacccgtt cggcgcgctg gccacggggc tgctggtgct c gccgggctg | 2460 |

-continued

```
gtggccgctt tcctggcgta ccggtacatt tcccgcctcc gcagcaaccc c atgaaggcg    2520 ctgtacccga tcaccacgcg cgcgctcaag gacgacgccc ggggcgcaac c gccccgggc    2580 gaggaagagg aggagtttga cgcggccaaa ctggagcagg cccgcgagat g atcaagtat    2640 atgtcgctcg tgtcagcggt cgagcggcaa gagcacaagg cgaaaaagag c aacaagggc    2700 ggcccgctgc tggcgacccg gctgacgcag ctcgcgcttc ggcggcgggc g ccgccggag    2760 taccagcagc ttccgatggc cgacgtcggg ggggcatga                            2799
```

<210> SEQ ID NO 2
<211> LENGTH: 30
<212> TYPE: DNA
<213> ORGANISM: Bovine herpesvirus 2

<400> SEQUENCE: 2

```
ttgtcgacat ggccgctcgc ggcggtgctg                                        30
```

<210> SEQ ID NO 3
<211> LENGTH: 21
<212> TYPE: DNA
<213> ORGANISM: Bovine herpesvirus 2

<400> SEQUENCE: 3

```
gcagggcagc ggctagcgcg g                                                 21
```

<210> SEQ ID NO 4
<211> LENGTH: 31
<212> TYPE: DNA
<213> ORGANISM: Bovine herpesvirus 2

<400> SEQUENCE: 4

```
aaactgcaga tgcaagggcc gacattggcc g                                      31
```

<210> SEQ ID NO 5
<211> LENGTH: 27
<212> TYPE: DNA
<213> ORGANISM: Bovine herpesvirus 2

<400> SEQUENCE: 5

```
atcttgtacc atatgaccgt ggcgttg                                           27
```

<210> SEQ ID NO 6
<211> LENGTH: 33
<212> TYPE: DNA
<213> ORGANISM: Bovine herpesvirus 2

<400> SEQUENCE: 6

```
aaaactgcag ggatggcggc aacagccatg agg                                    33
```

<210> SEQ ID NO 7
<211> LENGTH: 31
<212> TYPE: DNA
<213> ORGANISM: Bovine herpesvirus 2

<400> SEQUENCE: 7

```
cgcggatcct catttactaa aggaaagatt g                                      31
```

<210> SEQ ID NO 8
<211> LENGTH: 32
<212> TYPE: DNA
<213> ORGANISM: Bovine herpesvirus 2

-continued

<400> SEQUENCE: 8
aaaactgcag atgtccaacc atacccatca tc 32

<210> SEQ ID NO 9
<211> LENGTH: 35
<212> TYPE: DNA
<213> ORGANISM: Bovine herpesvirus 2

<400> SEQUENCE: 9
cgcggatccc tagatctgtg tagttgattg atttg 35

<210> SEQ ID NO 10
<211> LENGTH: 35
<212> TYPE: DNA
<213> ORGANISM: Bovine herpesvirus 2

<400> SEQUENCE: 10
aaaactgcag atgtccgaca caaaagcaga agggg 35

<210> SEQ ID NO 11
<211> LENGTH: 47
<212> TYPE: DNA
<213> ORGANISM: Bovine herpesvirus 2

<400> SEQUENCE: 11
cgcggatcct caataaaaat cattcccact gcgacttgaa acaaaac 47

<210> SEQ ID NO 12
<211> LENGTH: 32
<212> TYPE: DNA
<213> ORGANISM: Bovine herpesvirus 2

<400> SEQUENCE: 12
acgcgtcgac atgaagaaac tagagaaagc cc 32

<210> SEQ ID NO 13
<211> LENGTH: 33
<212> TYPE: DNA
<213> ORGANISM: Bovine herpesvirus 2

<400> SEQUENCE: 13
cgcggatcct cagccgggtt tgcaaactgg gag 33

<210> SEQ ID NO 14
<211> LENGTH: 36
<212> TYPE: DNA
<213> ORGANISM: Bovine herpesvirus 2

<400> SEQUENCE: 14
acgcgtcgac atgacgacta ctgcattcct ggtatg 36

<210> SEQ ID NO 15
<211> LENGTH: 33
<212> TYPE: DNA
<213> ORGANISM: Bovine herpesvirus 2

<400> SEQUENCE: 15
cgcggatcct cattgacgtc ccgaggtcat ttg 33

<210> SEQ ID NO 16
<211> LENGTH: 33
<212> TYPE: DNA
<213> ORGANISM: Bovine herpesvirus 2

```
<400> SEQUENCE: 16
tttgtcgaca tggaatattg gaaacacaca aac                                    33

<210> SEQ ID NO 17
<211> LENGTH: 33
<212> TYPE: DNA
<213> ORGANISM: Bovine herpesvirus 2

<400> SEQUENCE: 17
tttggatcct tagctgcagt ttttcggaac ttc                                    33

<210> SEQ ID NO 18
<211> LENGTH: 30
<212> TYPE: DNA
<213> ORGANISM: Bovine herpesvirus 2

<400> SEQUENCE: 18
tttgtcgaca tgatcatcac aaacacaatc                                        30

<210> SEQ ID NO 19
<211> LENGTH: 30
<212> TYPE: DNA
<213> ORGANISM: Bovine herpesvirus 2

<400> SEQUENCE: 19
tttggatcct cattgtctac ttgttagtac                                        30
```